United States Patent [19]

Edwards et al.

[11] Patent Number: 5,779,973

[45] Date of Patent: Jul. 14, 1998

[54] VAPOR PHASE INTERSTITIAL MICROBIAL DECONTAMINATION OF OVERWRAPPED IV BAGS

[75] Inventors: Steven Jay Edwards, Madison, Ohio; Paul Archie Steen, Apex, N.C.

[73] Assignee: Steris Corporation, Mentor, Ohio

[21] Appl. No.: 831,294

[22] Filed: Apr. 1, 1997

[51] Int. Cl.[6] .................................. A61L 2/00; A61L 9/00
[52] U.S. Cl. .......................... 422/28; 422/33; 422/292; 422/300
[58] Field of Search ........................ 422/28, 33, 292, 422/300, 306

[56] References Cited

U.S. PATENT DOCUMENTS

| Re. 33,007 | 8/1989 | Bier | 203/12 |
|---|---|---|---|
| 4,337,223 | 6/1982 | Kaye | 422/112 |
| 4,410,492 | 10/1983 | Kaye | 422/27 |
| 4,523,679 | 6/1985 | Paikoff et al. | 206/370 |
| 4,909,999 | 3/1990 | Cummings et al. | 422/298 |
| 5,348,711 | 9/1994 | Johnson et al. | 422/300 |
| 5,492,672 | 2/1996 | Childers et al. | 422/28 |
| 5,653,134 | 8/1997 | Bourne et al. | 422/26 |

*Primary Examiner*—Krisanne Thornton
*Attorney, Agent, or Firm*—Fay, Sharpe, Beall, Fagan, Minnich & McKee

[57] ABSTRACT

A vaporizer (48) vaporizes a liquid solution of hydrogen peroxide or other strong oxidants to form a sterilant vapor which is entrained in a flow of sterile air. The sterilant vapor is conveyed to a manifold (12), (36), (40). A plurality of tubes or conduits (14) convey the sterilant vapor from the manifold into a interstitial space (18) between an inner IV bag (24) and an outer overwrap (22). A vacuum pump (58) draws a negative pressure within an enclosure (42) to draw the sterilant vapor through the manifold, the delivery tubes, and the interstitial space and through the enclosure. The delivery tubes terminate opposite upper corners of the IV bag and are aimed in such a manner that the sterilant vapor gas flows through and contacts all surfaces which define the interstitial space. After sterilization, the sterilant vapor is displaced with sterile air and the IV bag assemblies are removed and the overwrap is sealed to prevent microbial recontamination.

16 Claims, 3 Drawing Sheets

VAPOR PHASE INTERSTITIAL MICROBIAL DECONTAMINATION OF OVERWRAPPED IV BAGS

BACKGROUND OF THE INVENTION

The present invention is directed to sterilization and decontamination. The invention finds particular application in connection with vapor phase sterilization by way of interstitial permeation to sterilize surfaces that define the interstitial space of an overwrapped IV bag and will be described with reference to such application. It will be appreciated, however, that the method and system of the present invention may be utilized in sterilizing a wide range of equipment and instruments.

Intravenous feeding assemblies typically include a sealed, fluid-filled vinyl IV bag and a plastic overwrap which protects the IV bag from contamination during shipping and while held in inventory. Steam is often used as a medium for decontaminating or sterilizing an outer surface of a liquid-filled vinyl IV bag that is sealed and wrapped in a plastic overwrap bag. However, during the steam decontamination or sterilization process, the plastic overwrap can become compromised as a result of either existing imperfections in the overwrap or damage incurred to the overwrap during handling at steam sterilization temperatures.

During steam sterilization, an excessive amount of moisture from condensation often becomes trapped between the IV bag and the overwrap. During the shelf life of an IV bag assembly, often two years, the presence of the moisture can support mold growth. Such growths render the assembly unusable scrap. There is currently no feasible method for efficiently removing the contaminated IV bag, placing it in a new plastic overwrap, and re-decontaminating or re-sterilizing the assembly to the desired $10^{-3}$ level.

Different levels of microbial decontamination are recognized in the art and by the Food and Drug Administration. For example, sanitizing connotes free from dirt or germs by cleaning. Disinfecting calls for cleansing in order to destroy harmful microorganisms. Sterilization, the highest level of biological contamination control, connotes the destruction of all living microorganisms and the ability to produce microorganisms. Sterilization, as used in this application, requires that fewer than $10^{-3}$ microorganisms in a test sample of microorganisms most resistant to a sterilization process survive the process.

A number of methods exist for effecting a $10^{-3}$ decontamination on an IV bag assembly. These known methods include the application of ETO (ethylene oxide), steam treatment, and the use of aseptic sealing materials. These methods have proven to be inefficient to recover the bulk of scrapped IV assemblies and are, in some instances, undesirable. For example, the use of pure concentrated ethylene oxide sterilant can be dangerous because it is explosive when mixed with oxygen both during and at the end of a cycle when air is admitted into the sterilization chamber. As a result, the ethylene oxide requires a diluent such as Freon, but Freon is undesirable because of its adverse effect on the ozone. Moreover, ethylene oxide is highly toxic to humans. It is typically absorbed in plastics and continues to degas long after the process is finished.

Vapor phase sterilization is a known useful technique for decontaminating or sterilizing the outer surfaces of reusable medical instruments, but the technique has not been adapted to interstitial sterilization. During vapor phase sterilization, medical instruments are placed in an enclosed space or chamber where sterilization occurs. The items to be sterilized are subjected to either a "deep vacuum" approach or a "flow through" approach. A liquid sterilant is vaporized in a heated vaporizer. Once vaporized, a deep vacuum is used to pull the sterilant vapor into the evacuated and sealed chamber. In the flow through approach, vaporized sterilant is mixed with a flow of carrier gas that delivers the sterilant vapor into, through and out of the chamber. The chamber may be at slightly negative or positive pressure.

For example, Bier, U.S. Pat. No. Re. 33,007, Aug. 1, 1989, incorporated herein by reference, discloses a method of vaporizing a multicomponent liquid, such as hydrogen peroxide and water, and passing the vapor in successive small increments into a sterilization chamber. Bier represents the deep vacuum approach to vapor phase sterilization.

Various other systems and apparatus have been developed for conducting vapor phase sterilization. An open flow through system designed to handle the disposition of residual sterilant vapors is disclosed in Cummings, et al., U.S. Pat. No. 4,909,999, Mar. 20, 1990, incorporated herein by reference. That system can be integrally associated with or releasably connected to a sealable container or other defined space to be decontaminated. Another flow through system is disclosed in Childers, U.S. Pat. No. 5,173,258, Dec. 22, 1992, incorporated herein by reference.

Vapor phase sterilization is a useful technique for sterilizing exterior surfaces of reusable medical instruments. It would be desirable to apply this technique to the sterilization of interstitial spaces and to ensure the flow of the vapor through the interstices contacts the walls or surfaces defining the space.

As materials costs continue to increase, coupled with the costs associated with disposal of bulk materials, it has become desirable and necessary to develop a method and system that provides complete and lasting interstitial sterilization of IV bag assemblies such that the overwrap bag can be sealed to avoid the possibility of recontamination in the interstitial spaces defined between the overlap and the inner bag. It is further desirable that the IV bag assemblies be suited to maintain the desired $10^{-3}$ level of sterilization during the assemblies' shelf life. It has also become desirable to develop a system and method that will adequately re-sterilize an assembly previously sterilized using a moisture based sterilant such as steam if any mold growth or other contamination occurs, for example, from moisture retention.

Finally, it is desirable that the method and system be applied or situated so that the overwrap may be sealed without a need for making contact with the sterilized surfaces and potentially contaminating them.

SUMMARY OF THE INVENTION

In a method of interstitial sterilization, an aqueous solution of a strong oxidant is vaporized to form a sterilant vapor. The sterilant vapor is delivered through at least one conduit which terminates in an interstitial space of an object to be sterilized. Sterilant vapor is flowed into the interstitial space to displace air and other gases therefrom. The sterilant vapor is maintained in contact with the surfaces defining the interstitial space until sterilization is achieved.

An IV bag assembly which includes an inner bag and an overwrap is microbially decontaminated. The IV bag assembly is suspended from a support within an enclosure such that the inner bag hangs freely within the overwrap to define a gas flow path between an outer surface of the inner bag and the inner surface of the overwrap of the IV assembly. A sterilant vapor is generated and directed through at least one conduit and into the gas flow path. Air in the gas flow path is replaced with the vapor, and the inner bag of the IV assembly is engulfed in the vapor. The vapor is held in the gas flow path until microbes on the outer surface of the inner bag and the inner surface of the overwrap are killed. The IV assembly is removed from the support and the overwrap is sealed.

A sterilization method for interstitial spaces of objects calls for suspending an object to be sterilized such that the interstitial space is open and clear to permit gas flow therethrough. A flow of sterilant mist into the interstitial space is provided, displacing ambient air therefrom. The sterilant mist is flowed through the interstitial space for a period of time sufficient to sterilize surfaces defining the interstitial space. A sterile gas is flowed through the interstitial space, and the sterilant mist is displaced. The object is removed from suspension and the interstitial space is sealed.

A system for microbially decontaminating an IV bag assembly includes an enclosure fluidly connected to a source of antimicrobial vapor. The system further includes a support which supports an IV bag assembly within the enclosure, and at least one conduit for directing the vapor from the vapor source to an interstitial space defined in the IV bag assembly.

One advantage of the present invention is that the interstitial sterilization provided to the IV bag is complete and lasting.

Another advantage of the present invention is that IV bag assemblies which were previously sterilized using a moisture based sterilant such as steam can be resterilized. Re-sterilization is particularly desirable in the event of any mold growth or other biological contamination.

Yet another advantage of the present invention is that the overwrap is sealed in such a manner that recontamination is avoided.

Still other advantages and benefits of the invention will become apparent to those skilled in the art upon a reading and understanding of the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE PREFERRED EMBODIMENTS

The IV bag may be positioned in a sterilizing chamber, or it may simply be shrouded under a tent, a hood or other covering. It is also possible that the sterilization could occur in ambient conditions provided there is a sufficient flow of sterilant vapor.

Figure 1:
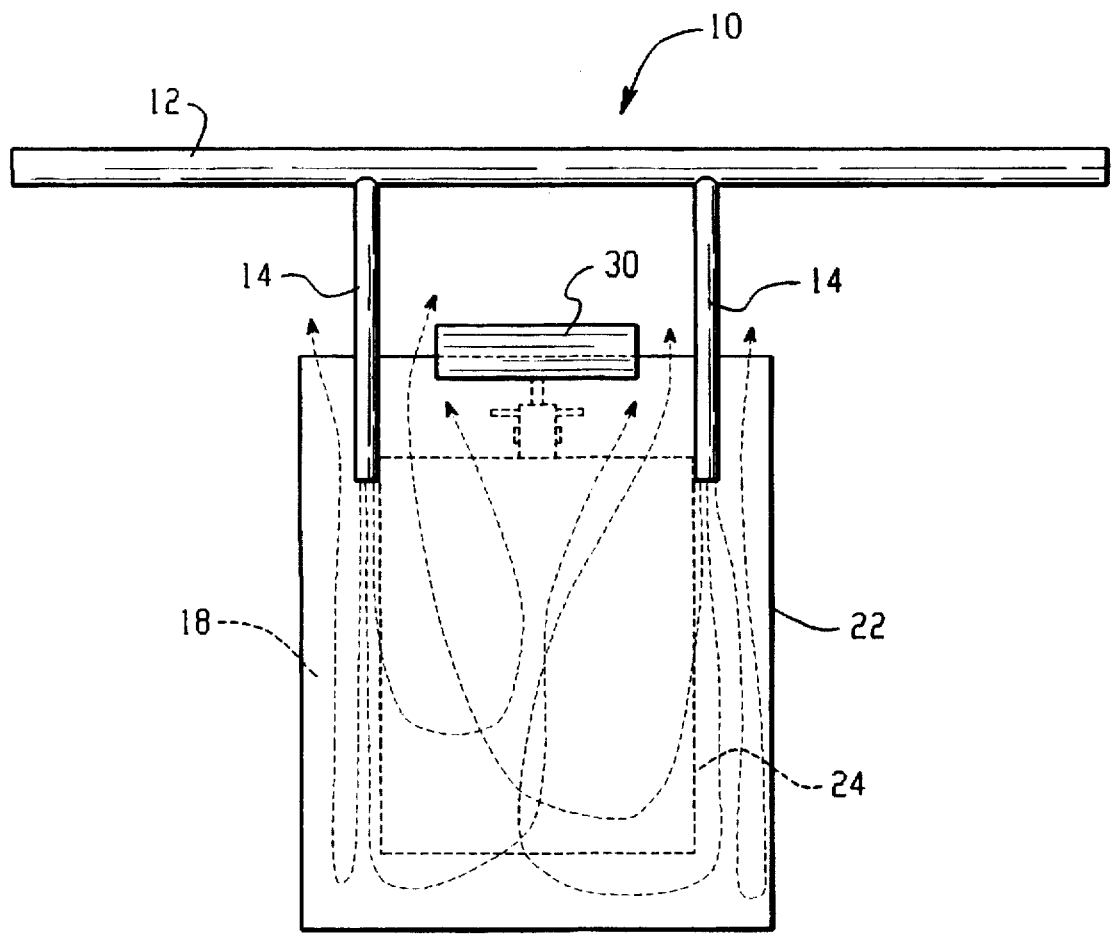
FIG. 1 is a diagrammatic illustration of an IV bag assembly support and sterilant vapor delivery system in accordance with the present invention.
Figure 2:
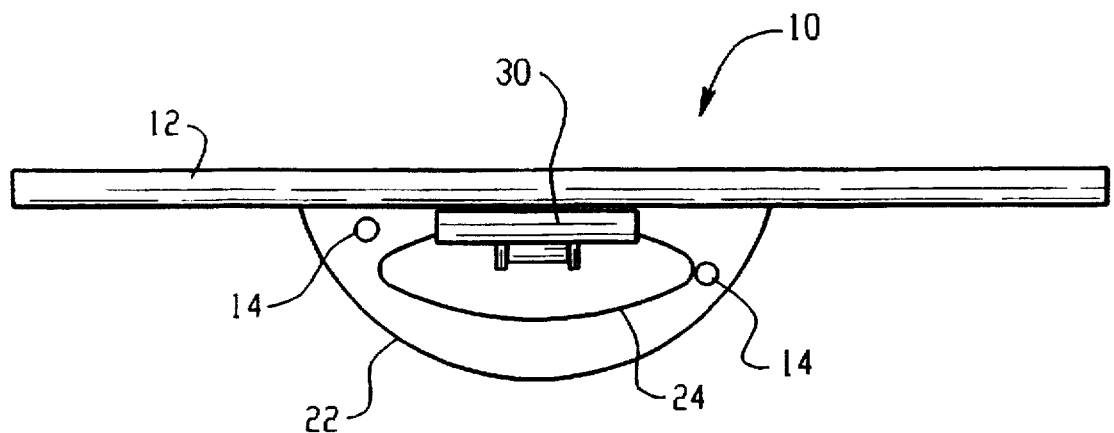
FIG. 2 is a top plan view of the embodiment shown in FIG. 1.

With reference to FIGS. 1 and 2, a sterilant vapor is generated or supplied and delivered to an IV bag/overwrap assembly 10 via a main delivery conduit 12 which branches into smaller, individual delivery tubes 14. The delivery tubes 14 are positioned within an interstitial space 18 defined by the inner surface of an overwrap 22 and the outer surface of an inner IV or other bag 24. The air inside the overwrap in the interstitial space is displaced and/or replaced with sterilant vapor flowing from the tubes 14. The inner bag 24 is positioned below the open edge of the outer bag, thereby allowing the sterilant vapor to engulf the inner bag completely. This inner bag position further ensures that the bottom of the inner bag is above the inner lower surface or bottom of the overwrap, thereby allowing a free flow of sterilant vapor in and around the bottom of the two bags.

Both the inner bag 24 and outer bag 22 are held in place by holding or supporting means or fixture 30. Preferably, the holding fixture is a sterile air or hydraulic clamping mechanism which permits a fully automated bag removal upon completion of the sterilization process to avoid any unnecessary handling of the sterilized surfaces. In lieu of air or hydraulic clamping mechanisms, mechanical clamps and fixed fingers, or other means, can be used to hold the inner and outer bags in position. Hydrogen peroxide sterilant vapor is preferably supplied or generated by a VHPO 1000 generator such as the generator described in U.S. Pat. No. 4,909,999, incorporated herein by reference.

Figure 3:
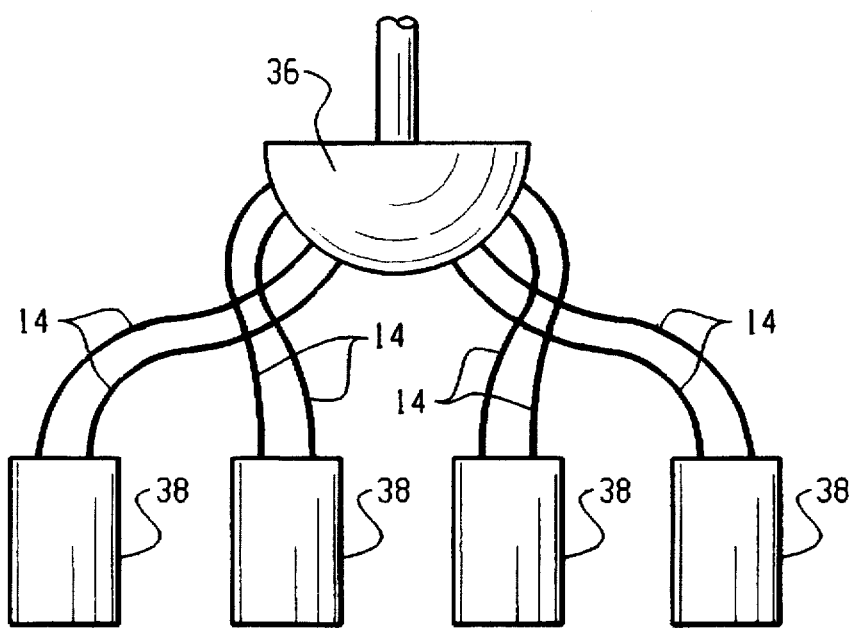
FIG. 3 is a diagrammatic representation of an alternative embodiment of the system for delivering a vapor phase sterilant to multiple IV bag assemblies.
Figure 4:
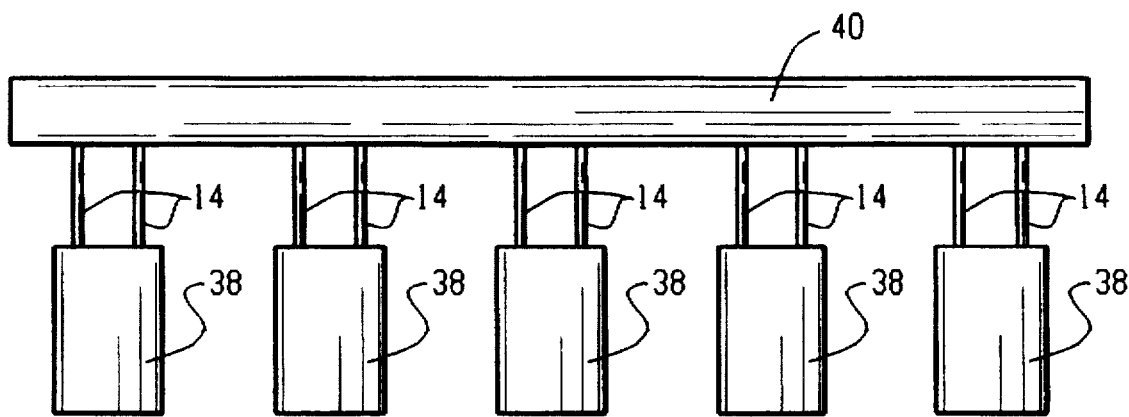
FIG. 4 is a diagrammatic view of another alternative embodiment.

Turning now to FIGS. 3 and 4, multiple IV bag assemblies can be sterilized simultaneously in accordance with the present invention. The process can be continuous or batch. With reference first to FIG. 3, a round sterilant vapor delivery manifold 36 directly supplies a series of IV bag assemblies 38. Multiple delivery tubes 14 deliver sterilant vapor directly from points circumferentially around the manifold 36 to the individual IV bag assemblies. Two separate delivery tubes join the manifold 36 with each IV bag assembly. Two tubes provide dual paths for the sterilant vapor to travel from the manifold to opposite sides of each individual IV bag assembly. Two opposite sterilant vapor introduction points adjacent opposite upper corners of the inner bag distribute the vapor and prevent dead zones over which the flow of vapor is not assured. The distributed vapor introduction assures sterilization of all parts of the interstitial space defined between the overwrap and the inner bag. Alternately, a single delivery tube with a forked or fanned end can distribute sterilant vapor around the interstitial space. Rather than permitting the vapor to flow out the open portions of the outer bag adjacent the clamp, an exit conduit can be inserted into the assembly to provide a controlled avenue for the discharge of displaced air and unspent sterilant.

In FIG. 4, an elongated sterilant vapor delivery manifold 40 is connected with a plurality of pairs of delivery tubes 14 which branch directly from the pipe. The delivery tubes direct sterilant vapor flow from the manifold to the individual IV bag assemblies. The vapor is introduced into spaced regions of the interstitial space to create a flow pattern which fully engulfs the inner bag during sterilization. Here again, air in the interstices is fully displaced by the sterilant vapor and all surfaces defining the interstices are contacted by the vapor and sterilized.

Due to the number of bags which require processing, it is desirable to obtain the optimum decontamination using the least air flow rate possible. One or more sterilant vapor generators effectively provides sterilant vapor to multiple IV bag assemblies at one time. For example, as shown in FIGS. 3 and 4, the sterilant vapor flow is diverted in any number of configurations to provide sterilant vapor to multiple decontamination sites.

Figure 5:
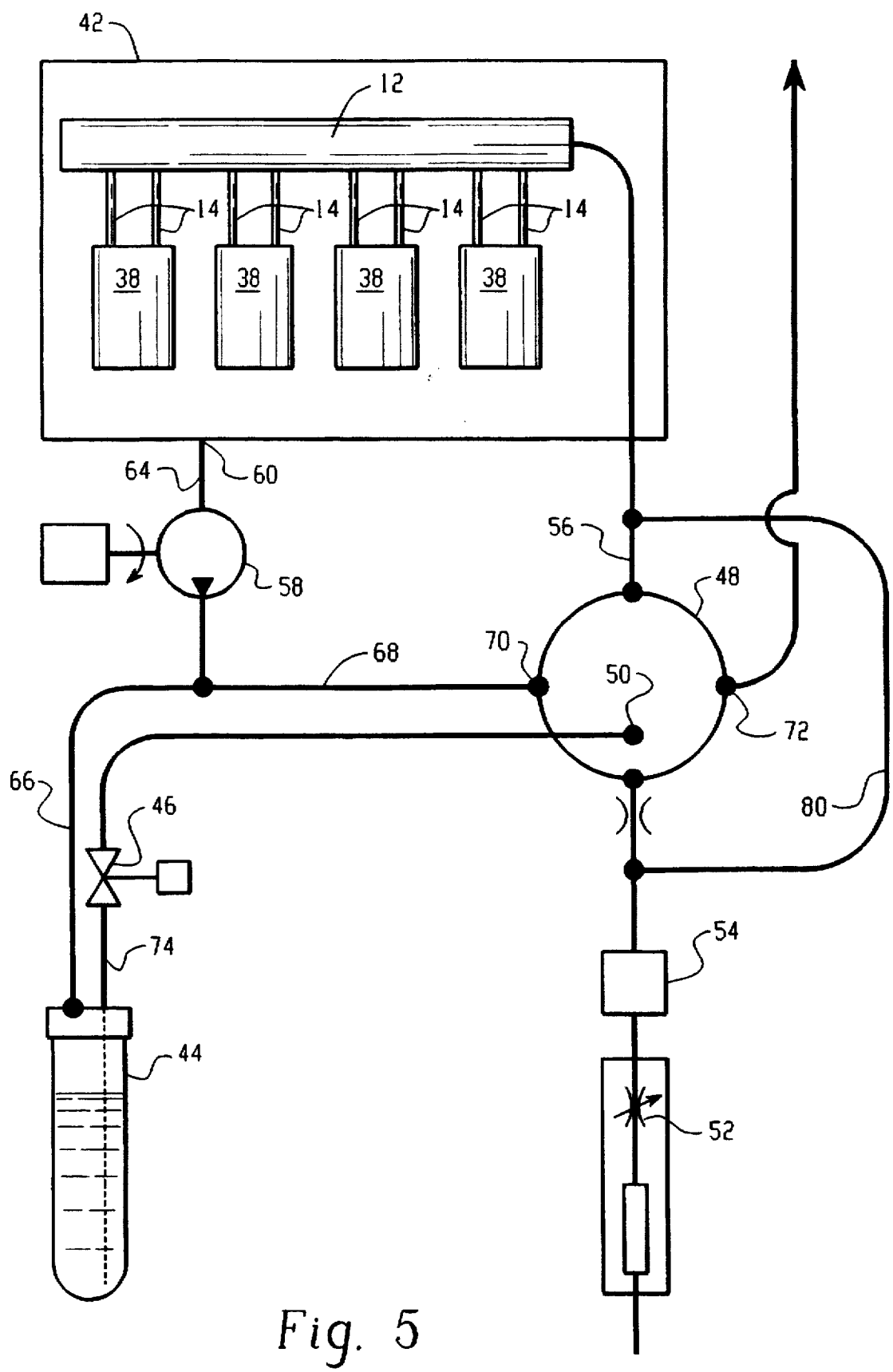
FIG. 5 is a diagrammatic illustration of an IV assembly sterilization system in combination with a flow through vapor phase hydrogen peroxide generator arrangement.

With reference to FIG. 5, the IV bag assemblies and the sterilant vapor distribution system of any of the preceding embodiments are disposed within the sterilization chamber or hood 42. The assemblies are mounted, for example, with the clamp assembly of FIGS. 1 and 2.

A strong oxidant in liquid solution is pumped from a reservoir 44 by a metering pump 46 to a vaporizer 48 at a controlled, metered rate. In the preferred embodiment, the strong oxidant is aqueous hydrogen peroxide solution having a concentration in the range of 3–98% by weight; preferably, from 5–98% by weight; and most preferably from 30–35% by weight. Other strong oxidants, such as peracetic acid, are also contemplated. In the vaporizer 48, the liquid sterilant solution is dripped or sprayed through a nozzle 50 onto a heated, catalytic plate which vaporizes the oxidant without breaking it down. Other vaporizing techniques such as ultrasonic vaporizers, atomizers, and the like are also contemplated.

As the sterilant vapor is formed, it is entrained in a carrier gas, preferably air, although other inert carrier gases are also contemplated. More specifically, an air flow regulator valve or baffle 52 controls a flow rate of air into the vaporizer. A filter system 54 filters the air to remove particulates. Preferably, the filter is sufficiently fine that microbes are removed as well as inert particulates. Preferably, a dehumidifier or other humidity and temperature control is also provided such that the gas received by the vaporizer has a controlled temperature, humidity, and cleanliness. The sterilant vapor entrained in the carrier gas is carried through an introduction tube or path 56 to the manifold 12, 36, 40.

As described above, the sterilant vapor flows from the manifold through each pair of tubes 14 into the interstitial space between the inner bag and the overwrap of each bag assembly 38. After flowing through the interstitial space, the sterilant vapor flows out the open tops of the overwrap assuring that all surfaces of the overwrap closure flaps are sterilized. The sterilant vapor cloud fills the chamber or hood 42 to control any microbial contamination on the exterior of tubes 14 or bag assemblies 38 to limit the inadvertent reintroduction of microbes into the overwrap during the sealing process.

A vacuum pump 58 provides a force which draws air from the chamber 42. A vacuum level within the chamber 42 is preferably kept low by the vacuum pump 58 to about 1.86–18.6 torr. Higher vacuums are also contemplated to the extent they are compatible with the items in the overwrap. As the pressure within the chamber 42 decreases, vacuum pump 58 ultimately draws air through the flow meter 52, the air filter 54, the vaporizer 48, the manifold, the delivery tubes 14, the interstitial space 18, and into the chamber 42. As the vacuum pump continues to operate, the air drawn through the vaporizer 48 into the chamber 42 flows through the chamber 42 and out through an exit 60 along a path 64 past vacuum pump 58. The exiting air stream is preferably split between paths 66 and 68. The path 66 is preferably narrower than path 68 so that a substantial portion of the stream of air flows along the path 68 to a portal 70 of the vaporizer 48 and out a portal 72 to exhaust. A remaining portion of air flows along path 66 and in combination with reduced pressure at the vaporizer creates a controlled pressure gradient to force liquid through path 74 and metering valve or pump 46 at the controlled rate.

The flow of sterilant vapor is directed through delivery conduit 12 and through delivery tubes 14. The flow of vapor phase sterilant continues for a time period suitable for sterilizing the interstitial spaces defined in the IV bag assemblies 38. Air displaced from the interstitial spaces is directed from the interstitial spaces and exits through the outlet 60.

The vapor phase sterilant is withdrawn from the chamber 42 and IV bag assemblies 38 through exit 60 along paths 64 and 68 through portal 70 and through vaporizer 44 where the sterilant is degraded and exhausted through portal 72. When hydrogen peroxide is used as the sterilant, the degraded components are harmless and can be vented to the atmosphere. When other gases, such as, for example, ethylene oxide or formaldehyde are used as the sterilant, and adequate means for destroying or recycling harmful gases are provided.

When no further sterilant entry into the chamber 42 or the IV bag assemblies is required, the injection valve 46 is closed. Vacuum pump 58 continues for a period sufficient to permit the sterile air stream to pass through the vaporizer 48 or a by-pass 80 to carry residual sterilant vapor from container 42 and the IV assemblies 38, to the vaporizer 48 for degradation.

Upon the completion of sterilization, each IV bag assembly is removed from the holding fixture. The overwrap is grasped mechanically or manually as the clamps are released. The overwrap is promptly closed and sealed without contacting any inner surfaces, hence contaminating, the inner interstitial surfaces.

When hydrogen peroxide vapor is the vapor chosen to sterilize the IV bag assemblies in accordance with the present invention, the concentration of hydrogen peroxide vapor is most preferably in the range of 1 to 5 milligrams per liter, preferably up to about 10 milligrams per liter, but may be higher, as long as condensation or saturation is avoided.

Various inert carriers, such as air, nitrogen or helium may be used with the sterilant vapor. The preferred embodiment employs a flow through approach, although the deep vacuum approach may be used as well. In using the flow through method, the carrier gas is preferably air, and the and the sterilant vapor is preferably a vapor phase hydrogen peroxide generated from aqueous hydrogen peroxide solution. As for the deep vacuum system, the sterilant vapor is preferably vapor phase hydrogen peroxide generated from aqueous hydrogen peroxide solution.

In an alternate, continuously conveyed embodiment, the chamber or hood 42 is constructed to permit the passage of solid articles through its end walls while blocking the flow of the sterilant vapor. For example, the sterile air can be pumped into higher pressure regions disposed at opposite ends of the chamber 42 to force the sterilant vapor to exit the chamber 42 at outlet 60. The manifold 12 is configured to move from a loading station through the chamber 42 to an unloading station. In one example, the manifold 12 is a circular ring which rotates on a central axis and the chamber 42 is accurate and extends about halfway around the ring. Other arrangements for moving the bag assemblies 38 through the chamber 42 while concurrently supplying gas thereto through the inlet tubes 14 are also contemplated.

The invention has been described with reference to the preferred embodiments. Obviously, modifications and alterations will occur to others upon a reading and understanding of this specification. It is intended to include all such modifications and alterations insofar as they come within the scope of the appended claims or the equivalents thereof.

Having thus described the preferred embodiment, the invention is now claimed:

1. A method for interstitial sterilization, comprising:

vaporizing an aqueous solution of a strong oxidant to form a sterilant vapor;

delivering the sterilant vapor through at least one conduit which terminates in an interstitial space between a sealed bag and an overwrap;

flowing sterilant vapor into the interstitial space displacing air and other gases therefrom;

maintaining the sterilant vapor in contact with an outer surface of the sealed bag and at least an inner surface of the overwrap which define the interstitial space until sterilization is achieved.

2. The method of claim 1 wherein the aqueous solution includes hydrogen peroxide with a concentration in the range of about 30–35% by weight.

3. The method of claim 1 including:

removing the object from the conduit and sealing the interstitial space to avoid contamination.

4. The method as set forth in claim 3 further including before the removing step:

flushing the sterilant vapor from the interstitial space with a sterile gas.

5. The method of claim 1 wherein the delivering step includes:

delivering the sterilant vapor through a plurality of conduits to a plurality of displaced regions of the interstitial space.

6. The method as set forth in claim 1 wherein the interstitial space is defined between a filled IV bag and an overwrap.

7. A method for microbially decontaminating an IV bag assembly which includes an inner bag and an overwrap, the method comprising:

suspending an IV bag assembly from a support within an enclosure such that the inner bag hangs freely within the overwrap to define a gas flow path between an outer surface of the inner bag and the inner surface of the overwrap of the IV assembly;

generating a sterilant vapor;

directing the vapor through at least one conduit and into the gas flow path;

replacing air in the gas flow path with the vapor;

engulfing the inner bag of the IV assembly in the vapor;

holding the vapor in the gas flow path until microbes on the outer surface of the inner bag and the inner surface of the overwrap are killed; and removing the IV assembly from the support and sealing the overwrap.

8. The method of claim 7 wherein the vapor includes a hydrogen peroxide vapor having a hydrogen peroxide concentration of about 30–35%.

9. The method of claim 7 wherein the sterilant vapor includes peracetic acid vapor.

10. The method of claim 7 including:

suspending a plurality of IV bag assemblies within the enclosure and directing the vapor through a plurality of conduits and into the flow paths defined within the plurality of IV bag assemblies.

11. The method of claim 7 wherein the directing step includes:

drawing a vacuum in the enclosure and using the vacuum to pull the vapor through the conduit and the gas flow path defined between the inner bag and the overwrap of the IV assembly.

12. A system for microbially decontaminating an IV bag assembly, the system comprising:

an enclosure fluidly connected to a source of antimicrobial vapor;

a support which supports an IV bag assembly within the enclosure;

at least one conduit for directing the vapor from said vapor source to an interstitial space defined in the IV bag assembly.

13. The system of claim 12 wherein the source of vapor includes a vaporizer which vaporizes a multicomponent liquid into a sterilant vapor.

14. The system of claim 12 wherein each IV bag assembly includes an inner bag and an overwrap with the interstitial space defined therebetween, the system further including:

a manifold connected with the anti-microbial vapor source for receiving the vapor therefrom;

a plurality of pairs of conduits connected with the manifold, each pair of conduits being positioned to extend into the interstitial space adjacent opposite upper corners of the inner bag for directing two flows of vapor into the interstitial space of each IV bag assembly.

15. The system of claim 12 further including a vacuum pump connected with the enclosure for drawing a negative pressure therein such that the vapor is drawn from the vaporizer, through at least one conduit, through the interstitial space defined in the IV bag assembly and into the enclosure.

16. A sterilization method for interstitial spaces between a fluid holding object and a surrounding overwrap, the sterilization method comprising:

suspending a fluid holding object and a surrounding overwrap such that the interstitial space between the fluid holding object and surrounding overwrap is open and clear to permit gas flow therethrough;

providing a flow of sterilant mist into the interstitial space displacing ambient air therefrom;

flowing the sterilant mist through the interstitial space for a period of time sufficient to sterilize surfaces defining the interstitial space;

flowing a sterile gas through the interstitial space displacing the sterilant mist;

removing the fluid holding object and surrounding overwrap from suspension and sealing the interstitial space.

* * * * *

UNITED STATES PATENT AND TRADEMARK OFFICE
CERTIFICATE OF CORRECTION

PATENT NO. : 5,779,973

DATED : July 14, 1998

INVENTOR(S) : Steven Jay Edwards, et al.

It is certified that error appears in the above-identified patent and that said Letters Patent is hereby corrected as shown below:

Column 7, line 22, delete "object" and insert --sealed bag and overwrap--

Signed and Sealed this

Eighteenth Day of May, 1999

*Attest:*

Q. TODD DICKINSON

*Attesting Officer*     *Acting Commissioner of Patents and Trademarks*